United States Patent [19]

Ichikawa et al.

[11] 4,145,366

[45] Mar. 20, 1979

[54] PROCESS FOR ISOMERIZING ONE OF THE GEOMETRIC ISOMERS OF AN α,β-UNSATURATED ALDEHYDE TO ITS CORRESPONDING OTHER GEOMETRIC ISOMER

[75] Inventors: Yataro Ichikawa, Iwakuni; Teizo Yamaji, Yamaguchi, both of Japan

[73] Assignee: Teijin Limited, Osaka, Japan

[21] Appl. No.: 843,341

[22] Filed: Oct. 18, 1977

Related U.S. Application Data

[63] Continuation of Ser. No. 633,083, Nov. 18, 1975, abandoned.

[30] Foreign Application Priority Data

Nov. 18, 1974 [JP] Japan .............................. 49-131989
Nov. 18, 1974 [JP] Japan .............................. 49-131990

[51] Int. Cl.$^2$ ............................................. C07C 47/20
[52] U.S. Cl. ............................. 260/601 R; 260/347.8; 260/601 H
[58] Field of Search .................... 260/601, 598, 615 R, 260/602, 601 H, 347.8, 601 R; 560/177

[56] References Cited

U.S. PATENT DOCUMENTS 3,210,427  10/1965  Redel et al. ......................... 260/598

OTHER PUBLICATIONS

Handbook of Physics & Chemistry, 54th edition.
Hubbard "J. Amer. Chem. Society", vol. 78 (1956, pp. 4662-4667.

*Primary Examiner*—Werren B. Lone
*Attorney, Agent, or Firm*—Wenderoth, Lind & Ponack

[57] ABSTRACT

Process for preparing a trans-α,β-unsaturated aldehyde or a cis-α,β-unsaturated aldehyde at high conversions and selectivities, which comprises isomerizing a cis-α,β-unsaturated aldehyde to its corresponding trans-α,β-unsaturated aldehyde or vice versa by heating the starting aldehyde at a temperature of 30° to 400° C. in the presence of an acid catalyst having a pKa of 1 to 7 in the presence or absence of a solvent. If desired, the resulting isomerization mixture can be separated into the constituent geometric isomers. The isomerization mixture or the separated isomers can be used as pharmaceuticals, their intermediates, or essential ingredients of perfumes and cosmetics.

16 Claims, No Drawings

PROCESS FOR ISOMERIZING ONE OF THE GEOMETRIC ISOMERS OF AN α,β-UNSATURATED ALDEHYDE TO ITS CORRESPONDING OTHER GEOMETRIC ISOMER

This is a continuation of application Ser. No. 633,083, filed Nov. 18, 1975, now abandoned.

This invention relates to a process for isomerizing one of the geometric isomers of an α,β-unsaturated aldehyde to the corresponding other geometric isomer. More specifically, it relates to a process for preparing a trans-α,β-unsaturated or a cis-α,β-unsaturated aldehyde which comprises isomerizing a cis-α,β-unsaturated aldehyde to a trans-α,β-unsaturated aldehyde, the corresponding geometric isomer, or vice versa, and if desired, separating the trans-α,β-unsaturated aldehyde and the cis-α,β-unsaturated aldehyde from the resulting isomerization reaction mixture.

Conventional techniques for cis-trans stereoisomerization of α,β-unsaturated aldehyde typically include the following two methods.

(A) A method which comprises treating retinene in the presence of light using iodine as a catalyst under shielding of air [J. Am. Chem. Soc. 78, 4662 (1956)].

(B) A method which comprises treating a retinene isomeric mixture in the presence of a strong acid such as hydrochloric acid, sulfuric acid or p-toluenesulfonic acid and a complex-forming compound such as pyrocatechol at a temperature of as low as −10° C. to 25° C. (U.S. Pat. No. 3,210,427 and British Pat. No. 936,564).

The method (A) however, has the defect that the product is decomposed by traces of hydrogen iodide which is formed readily from iodine remaining in the product (see U.S. Pat. No. 3,838,029 and British Pat. No. 1,394,474), and it is extremely difficult to separate the decomposition product from the final product.

According to the method (B), side reactions such as cyclization occur because of using the strong acid, and the corrosion of the equipment is heavy. Hence, this method is not industrially advantageous. As regards the cyclization reaction, Industrial and Engineering Chemistry, Vol. 40, No. 2, page 260 (1948) reported that when citral is treated in ethyl acetate with 50% sulfuric acid, dehydropulegol and dehydroisopulgol are formed. This reaction is expressed by the following reaction scheme.

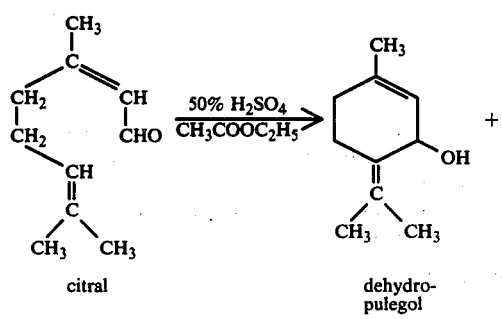

citral    dehydro-
          pulegol

-continued

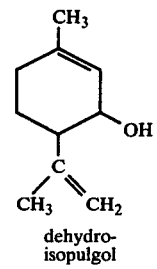

dehydro-
isopulgol

In an attempt to remove these defects of the conventional methods, we made extensive investigations. Our efforts finally led to the discovery that by maintaining one of the geometric isomers of an α,β-unsaturated aldehyde at a temperature of 30° to 400° C. in the presence of an acid having a pKa of 1 to 7, preferably 1.2 to 6, it can be isomerized to the corresponding other geometric isomer at a high selectivity, and therefore, by separating both geometric isomers (cis-isomer and trans-isomer) from the resulting isomerization reaction mixture by a suitable method, one or both of the geometric isomers can be recovered at a high selectivity.

The invention will be described in detail hereinbelow.

The α,β-unsaturated aldehyde used as a starting material in this invention is expressed by the following formula (1-A) or (1-B).

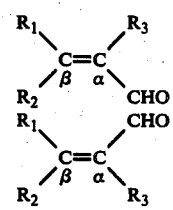

In the formulae (1A) and (1B), $R_1$ is a residue of a saturated or unsaturated hydrocarbon; $R_2$ and $R_3$ are identical or different and each represents a hydrogen atom, a residue of a saturated or unsaturated hydrocarbon or a heterocyclic group, and $R_2$ is different from $R_1$; each of $R_1$, $R_2$ and $R_3$ may form a heterocyclic group via an oxygen, sulfur or nitrogen atom; and the hydrocarbon residue or heterocyclic group represented by $R_1$, $R_2$ or $R_3$ may have 1 to 3 alkoxy groups containing not more than 5 carbon atoms, 1 to 3 alkoxycarbonyl groups containing not more than 6 carbon atoms or 1 to 3 halogen atoms as substituents.

A mixture of the geometric isomers of an α,β-unsaturated aldehyde expressed by the above formulae (1-A) and (1-B) may also be used as the starting material.

Since $R_1$ is different from $R_2$ in the formulae (1-A) and (1-B), the α,β-unsaturated aldehyde of formula (1-A) and the α,β-unsaturated aldehyde of formula (1-B) are corresponding geometric isomers.

When one of the geometric isomers of the α,β-unsaturated aldehyde or a mixture of both isomers is heated to a temperature of 30° to 400° C. in the presence of an acid having a pKa of 1 to 7, the isomer (for example, trans-isomer) of formula (1-A) is isomerized to the isomer (for example, cis-isomer) of formula (1-B) or vice versa until a certain equilibrium state expressed by the following formula (2) is reached.

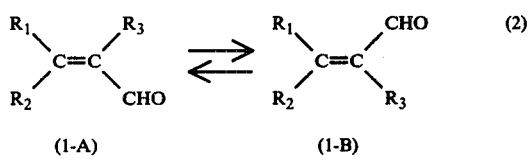

(1-A)    (1-B)

The above equilibrium state changes according to various factors such as the starting aldehyde to be isomerized or the heating temperature.

According to this invention, one of the geometric isomers of the α,β-unsaturated aldehyde can be isomerized to the corresponding other isomer by the above isomerization reaction, and the isomerization reaction mixture can be used, either directly or after purification, as pharmaceuticals or their intermediates or essential ingredients of perfumes or cosmetics. If desired, the two geometric isomers may be separated and recovered from the isomerization reaction mixture by suitable conventional methods, and used separately for the above-mentioned purposes.

For the above reason, a mixture of the geometric isomers may be used as the starting material, and the process of the invention makes it possible to change the ratio of the geometric isomers in the mixture. If desired, the individual isomers can be separated from the reaction mixture.

Preferred species of the α,β-unsaturated aldehyde used in this invention are those of formula (1-A) and/or formula (1-B) wherein $R_1$, $R_2$ and $R_3$ contain not more than 50, preferably not more than 30, carbon atoms and each represents an alkyl group, an alkenyl group, an alkynyl group, an alicyclic group, an aromatic group, a heterocyclic group containing an oxygen, sulfur or nitrogen atom, a group formed by bonding at least two of these groups, or a heterocyclic group formed by bonding at least two of these groups through an oxygen, sulfur or nitrogen atom. Those in which $R_1$, $R_2$ and $R_3$ contain not more than 50, preferably not more than 30, carbon atoms and each represents a group selected from alkyl, alkenyl, alicyclic and aromatic groups are especially preferred. In this case, one or both of $R_2$ and $R_3$ may be a hydrogen atom, and $R_1$, $R_2$ and $R_3$ may be substituted. Examples of the substituent are alkoxy groups containing not more than 5 carbon atoms such as methoxy, ethoxy, n-propoxy, iso-propoxy, butoxy or pentoxy, alkoxycarbonyl groups containing not more than 6 carbon atoms such as methoxycarbonyl, ethoxycarbonyl, n-propoxycarbonyl, butoxycarbonyl or pentoxycarbonyl, and halogen atoms such as fluorine, chlorine or bromine. Each of $R_1$, $R_2$ and $R_3$ may be substituted by 1 to 3 such substituents.

In particular, it is preferred to use α,β-unsaturated aldehydes of formula (1-A) and/or formula (1-B) in which $R_1$ is an alkyl group containing 1 to 30 carbon atoms or an alkenyl group containing 2 to 30 carbon atoms, and $R_2$ and $R_3$ represent a hydrogen atom or an alkyl group containing 1 to 5 carbon atoms.

Specific examples of the α,β-unsaturated aldehydes that can be used in this invention are given below. It should be noted however that the invention is in no way limited to them.

(1) Aliphatic aldehydes 3-ethyl-buten-2-al-1, 3-propylbuten-2-al, 3-butylbuten-2-al-1, 3,3-ethylpropyl-acrolein, 2-ethylhexen-2-al-1, 2-ethylisohexen-2-al-1, 2,6-nonadienal, 2-n-amyl-crotonaldehyde, 2-hexyl-crotonaldehyde, 2-propylideneenanthaldehyde, 2-octylcrotonaldehyde, citral, diisovaleraldehyde, dihydrocitral, 6-methylcitral, citrylideneacetaldehyde, citrylidenepropyonaldehyde, farnesal, and geranyl geranial.

(2) Alicyclic aldehydes

Cyclocitrylideneacetaldehyde, cyclocitrylidenepropionaldehyde, methylional, ionylideneacetaldehyde, Vitamine A aldehyde, dihydroretinal, and tetrahydroretinal.

(3) Aromatic aldehydes

Cinnamaldehyde, nuciferal, 2-ethylcinnamaldehyde, 2-isopropylcinnamaldehyde, 2-n-butylcinnamaldehyde, 2-hexylcinnamaldehyde, p-methylcinnamaldehyde, 2-methyl-2-isopropylphenyl acrolein, 5-phenyl-2-penten-1-al and benzylidene citronellal.

(4) Heteroaldehyde

2-Methyl-3-furyl-acrolein, 2-ethyl-3-furyl-acrolein, 2-propyl-furyl-acrolein, 3-methyl-4-furylidene-butyraldehyde, and 5-(2-furyl)-3-methyl-2-pentenal.

Of these aldehydes, the aldehydes exemplified in (1) and (2), especially the aliphatic α,β-unsaturated aldehydes mentioned in (1) are most preferred.

Generally, the reaction in this invention is carried out preferably in the liquid phase either in the presence of absence of an organic solvent. The use of solvent, however, is advantageous. The organic solvent is preferably a neutral inert organic solvent which can dissolve the α,β-unsaturated aldehyde or is miscible with it. Preferably, the organic solvent contains water in an amount of not more than 25% by weight, especially not more than 20% by weight, most preferably not more than 10% by weight. Examples of preferred organic solvents are shown below.

(1) Aliphatic hydrocarbons

Propane, butane, pentane, hexane, heptane, octane, petroleum ether, and ligroin.

(2) Alicyclic hydrocarbons

Cyclohexane, methylcyclohexane, ethylcyclohexane and decalin.

(3) Aromatic hydrocarbons benzene, toluene, xylene (o-, m- and p-), cumene and tetralin.

(4) Halogenated hydrocarbons

Carbon tetrachloride, methylene chloride, chloroform, dichloroethane, trichloroethane, tetrachloroethane, chlorobenzene, dichlorobenzene, and perchloroethylene.

(5) Ethers

Diethyl ether, tetrahydrofuran, dioxane and monoglyme.

(6) Esters

Ethyl acetate, butyl acetate, methyl benzoate, dimethyl phthalate, diethyl phthalate, and dibutyl phthalate.

(7) Ketones

Acetone, methyl ethyl ketone, dibutyl ketone and cyclohexanone.

(8) Alcohols

Methanol, ethanol, n-propanol, isopropanol, n-butanol, isobutanol, t-butanol, n-amyl alcohol, isoamyl alcohol, cyclohexanol, and phenylethyl alcohol.

Of these, the aliphatic hydrocarbons (1), the alicyclic hydrocarbons (2), the aromatic hydrocarbons (3), the alcohols (8), and the esters (6) are preferred. Especially preferred species are those which are liquid at room temperature and contain not more than 15 carbon atoms.

When the solvent is used, its amount is 0.01 to 200 parts by weight, preferably 0.1 to 100 parts by weight, per part by weight of the $\alpha,\beta$-unsaturated aldehyde starting material.

The acid used as a catalyst in this invention has an acid strength (pKa) of 1 to 7, preferably 1.2 to 6. When acids having a pKa of less than 1 are used, side-reactions such as cyclization occur markedly, and the selectivity is reduced. On the other hand, when acids having a pKa of more than 7 are used, the isomerization reaction does not substantially take place.

Any inorganic acids or organic acids which are either liquid or solid can be used in this invention so long as they have a pKa within the above-specified range. Accordingly, as will be shown later in working examples, the acid may be an ion exchange resin having a pKa within the above-specified range.

The method of measuring the pKa of the acid is disclosed, for example, in "Dissociation Constants of Organic Acids in Aqueous Solution", by G. Kortum, W. Vogel and K. Andrussow; Butterworths; London (1961).

Specific examples of the acid catalyst are in organic acids such as hydrofluoric acid, nitrous acid, chromic acid, selenic acid, telluric acid, hypophosphorus acid, phosphorus acid, and phosphoric acid, and zinc hydroxide, and organic acids such as aliphatic carboxylic acids (e.g., formic acid, acetic acid, butyric acid, valeric acid, monochloroacetic acid, fluoroacetic acid, acrylic acid, trimethylacetic acid, or tartaric acid), alicyclic carboxylic acids (e.g., cyclohexanecarboxylic acid, cyclohexanedicarboxylic acid, cyclobutanedicarboxylic acid, cyclopropanedicarboxylic acid, cyclopentanedicarboxylic acid, or methylcyclohexanecarboxylic acid), and aromatic carboxylic acids (e.g., benzoic acid, o-, m- or p-toluic acid, phthalic acid, isophthalic acid, terephthalic acid, trimellitic acid, $\alpha$- or p-naphthoic acid, anisic acid, o-, m- or p-chlorobenzoic acid, or o-, m- or p-bromobenzoic acid). Cation-exchange resins having, for example, a carboxyl group as an acid site and having a pKa of 1 to 7, preferably 1.2 to 6, can also be used.

Partial esters of the inorganic and organic acids can also be used. The partial esters of the inorganic acids are, for example, the partial esters of polybasic inorganic acids such as monoethyl phosphate, diethyl phosphate, di-n-butyl phosphate, diethyl phosphite, dibutyl phosphite, diphenyl phosphate or diethyl hypophosphite. The partial esters of the organic acids include, for example, the partial esters of polybasic organic carboxylic acids such as monomethyl terephthalate, monomethyl isophthalate, monoethyl phthalate, monoethyl oxalate, monoethyl malonate, monomethyl adipate, monomethyl fumarate, monomethyl trimellitate or dimethyl trimellitate.

Especially preferred acid catalysts are those which are soluble in the reaction system and are selected from the inorganic acid, the partial esters of the inorganic acids, organic carboxylic acids containing not more than 10 carbon atoms and the partial esters of the organic carboxylic acids.

These catalysts can be used either alone or as a mixture of two or more.

The amount of the acid catalyst used in this invention can be varied according, for example, to the reaction temperature and the reaction time. Generally, it is at least $10^{-5}$ mole, preferably at least $10^{-4}$ mole, more preferably at least $10^{-3}$ mole, per mole of the $\alpha,\beta$-unsaturated aldehyde. There is no particular upper limit to the amount of the catalyst, but from an economic viewpoint, the amount of the catalyst is up to 10 moles, especially up to 1 mole, per mole of the aldehyde.

By using the acid catalyst having an acid strength, pKa, of 1 to 7, preferably 1.2 to 6, in the amount specified above, the $\alpha,\beta$-unsaturated aldehyde can be isomerized at a high selectivity with the inhibition of side-reactions.

Our investigations show that relatively high temperatures are effective for the isomerization in accordance with this invention, and at such temperatures, trans- or cis-$\alpha,\beta$-unsaturated aldehydes can be obtained at high conversions and selectivities within short periods of time. Generally, the reaction temperature is 30° to 400° C., more 30° to 350° C., preferably 40° to 300° C., especially preferably 50° to 250° C.

The reaction time differs according, for example, to the reaction temperature or the amount of the catalyst, but is generally 1 second to 100 hours, preferably 1 minute to 50 hours, more preferably 5 minutes to 20 hours.

The reaction in accordance with this invention can be performed at atmospheric, elevated or reduced pressures. The reaction is preferably carried out in an atmosphere of an inert gas such as nitrogen or hellium, and either a continuous process or a batchwise process can be employed.

The following Examples further illustrate the present invention. Unless otherwise specified, all parts in the examples are by weight. The various analysis values given in the examples were measured by the methods indicated below.

The infrared absorption spectrum was measured by a Shimazu IR-27-G diffraction grating type device using a KBr plate as a cell. The NMR data were obtained by means of Nippon Denshi GNM-MH-100 (100 MHz) using carbon tetrachloride as a solvent. The molecular weights and elemental analysis values were determined by a high resolving power mass spectrum measured with a Nippon Denshi JMS-D-100 Model mass spectrometer. The quantitative analysis of the reaction results was performed by gas chromatography using a Yanagimoto G-8-Model gas-chromatogram.

EXAMPLE 1

(1) Commercially available natural citral (purity 98% or more) was distilled by a spinning band rectification device. A fraction having a boiling point of 50° to 51° C./0.15 mmHg was collected. Analysis of this fraction by infrared absorption spectrum, high resolving power mass spectrum and nuclear magnetic resonance spectrum led to the confirmation that it was cis-citral.

(2) Then, 25 parts of the cis-citral was reacted at 150° C. for 3 hours in an atmosphere of nitrogen using 100 parts of substantially anhydrous isopropyl alcohol as a solvent and 1 mole%, based on the cis-citral, of phthalic acid as a catalyst. The phthalic acid was neutralized with alkali, and the isopropyl alcohol was distilled off at reduced pressure. The distillation residue was washed twice with 50 parts of water and then with a weak aqueous alkali solution. The washed residue was dried for one day with Glauber's salt. The citral obtained was distilled by a Widmer rectification device, and then by a spinning band rectification device to afford 10.1 parts of a fraction having a boiling point of 50° to 51° C./0.15 mmHg (fraction A) and 13.9 parts of a fraction having a boiling point of 67° to 68° C./1.2 mmHg (fraction B). Analysis of these fractions led to the confirmation that fraction (A) was cis-citral and fraction (B) was trans-citral. The results of analyses are shown in Table 1.

Table 1

| Structure | B.P. °C./mmHg | High-mass data Calculated | High-mass data Found | Infrared spectrum (specific absorption) (cm$^{-1}$) | NMR spectrum (specific absorption) $\tau$ value | H number |
|---|---|---|---|---|---|---|
| cis-citral | 50–51/0.15 | C$_{10}$H$_{16}$O 152.1201 | C$_{10}$H$_{16}$O 152.1284 | $v_{c=o}$ 1675 $v_{c=c}$ 1632 1162, 840 | H(a) 0.00 0.08(d) H(b) 4.08 4.18(d) H(c) 8.00(s) | 1 1 3 |
| trans-citral | 67–68/1.2 | C$_{10}$H$_{16}$O 152.1201 | C$_{10}$H$_{16}$O 152.1226 | $v_{c=o}$ 1675 $v_{c=c}$ 1635 1613 1192, 1120 815 | H(a) −0.08 0.00(d) H(b) 4.08 4.16(d) H(c) 7.76 7.84(d) | 1 1 3 |

EXAMPLES 2 to 13

0.25 part of cis-citral was reacted at 150° C. for 3 hours in an atmosphere of nitrogen using 1 part of substantially anhydrous isopropanol as a solvent and 1 mole%, based on the citral, of each of the various catalysts shown in Table 2. The resulting reaction mixture was separated into cis-citral (retention time, 6.5 minutes) and trans-citral (retention time, 7.8 minutes) by a gas-chromatographic analysis (internal reference method) under the following conditions:

carrier: GLC-100
column: PEG 20 M, 75 cm
initial temperature: 70° C.
rate of temperature rise: 4° C./min.
carrier gas: helium 30 ml./min.

The conversion of cis-citral and the selectivity of trans-citral were measured in accordance with the following equations.

$$\text{Conversion of cis-citral} = \frac{\left(\begin{array}{c}\text{cis-citral}\\\text{charged}\end{array}\right) - \left(\begin{array}{c}\text{remaining}\\\text{cis-citral}\end{array}\right)}{\text{cis-citral charged}} \times 100\,(\%)$$

$$\text{Selectivity of trans-citral} = \frac{\text{trans-citral produced}}{\left(\begin{array}{c}\text{cis-citral}\\\text{charged}\end{array}\right) - \left(\begin{array}{c}\text{remaining}\\\text{cis-citral}\end{array}\right)} \times 100\,(\%)$$

The results are shown in Table 2.

Table 2

| Example | Catalyst Kind | pKa | Conversion of cis-citral (%) | Selectivity of trans-citral (%) |
|---|---|---|---|---|
| 2 | Phthalic acid | 2.95 | 58.9 | 96.3 |
| 3 | Terephthalic acid | 3.54 | 39.5 | 96.7 |
| 4 | Benzoic acid | 4.20 | 24.9 | 83.5 |
| 5 | Acetic acid | 4.76 | 24.0 | 89.2 |
| 6 | Oxalic acid | 1.2 | 60.5 | 90.5 |
| 7 | Pivalic acid | 5.03 | 12.0 | 90.6 |
| 8 | Phosphorous acid | 1.8 | 57.2 | 87.0 |
| 9 | Hypophosphorous acid | 1.0 | 55.4 | 94.2 |
| 10 | Diethyl phosphite | 4.0 | 45.0 | 97.4 |
| 11 | n-Dibutyl phosphate | 1.5 | 56.8 | 88.6 |
| 12 | Phosphoric acid | 2.15 | 54.4 | 93.8 |
| 13 | Ion-exchange resin (IRC-50) | 4~5 | 13.2 | ~100 |

EXAMPLES 14 to 22

0.25 part of trans-citral was reacted at 150° C. for 3 hours in an atmosphere of nitrogen using 1-part of substantially anhydrous isopropanol as a solvent and 1 mole%, based on the trans-citral, of each of the catalysts shown in Table 3. After the reaction, the ratio of the cis- to trans-citral was measured in the same way as in Examples 2 to 13, and the conversion of trans-citral and the selectivity of cis-citral were determined. The results are shown in Table 3.

Table 3

| Example | Catalyst Kind | pKa | Conversion of trans-citral (%) | Selectivity of cis-citral (%) |
|---|---|---|---|---|
| 14 | Oxalic acid | 1.2 | 39.0 | 90.0 |
| 15 | Phthalic acid | 2.95 | 40.3 | 89.3 |
| 16 | Terephthalic acid | 3.54 | 20.9 | 100.0 |
| 17 | Benzoic acid | 4.2 | 15.0 | 92.7 |
| 18 | Pivalic acid | 5.0 | 10.0 | 90.6 |
| 19 | Phosphoric acid | 2.15 | 41.3 | 80.0 |
| 20 | Hypophosphorous acid | 1.0 | 43.1 | 80.0 |
| 21 | Diethyl hypophosphite | 4.0 | 35.4 | 84.2 |
| 22 | Di-n-butyl phosphate | 1.5 | 42.4 | 84.0 |

EXAMPLES 23 TO 31

0.25 part of trans-citral was reacted in an atmosphere of nitrogen at the temperature and for the time periods indicated in Table 4 using 1 part of substantially anhydrous isopropanol as a solvent and 1 mole%, based on the trans-citral, of phthalic acid as a catalyst.

In Examples 29 and 30, ethylbenzene was used instead of the isopropanol, and in Example 31, n-dodecane was used instead of the isopropanol. The results are shown in Table 4.

Table 4

| Example | Reaction temperature (° C.) | Reaction time (hours) | Conversion of trans-citral (%) | Selectivity of cis-citral (%) |
|---|---|---|---|---|
| 23 | 50 | 20 | 10.0 | 100.0 |
| 24 | 70 | 20 | 22.3 | 100.0 |
| 25 | 130 | 3 | 39.3 | 89.5 |
| 26 | 200 | 3 | 44.4 | 64.0 |
| 27 | 250 | 1/6 | 40.9 | 61.4 |
| 28 | 300 | 1/6 | 55.4 | 35.2 |
| 29 | 300 | 1/30 | 21.9 | 92.3 |
| 30 | 350 | 1/160 | 25.1 | 82.1 |
| 31 | 370 | 1/120 | 25.3 | 80.2 |

EXAMPLES 32 TO 40

The procedure of Examples 23 to 31 was repeated at the temperatures and for the time periods indicated in Table 5 using cis-citral as starting material instead of the trans-citral and each of the various solvents indicated in Table 5. The results are shown in Table 5.

Table 5

| Ex. | Solvent | Reaction temperature (° C.) | Reaction time (hours) | Conversion of cis-citral (%) | Selectivity of trans-citral (%) |
|---|---|---|---|---|---|
| 32 | isopropanol | 200 | 3 | 68.2 | 78.1 |
| 33 | isopropanol | 130 | 3 | 58.2 | 96.9 |
| 34 | isopropanol | 50 | 20 | 19.0 | 99.0 |
| 35 | isopropanol | 70 | 20 | 49.1 | 99.0 |
| 36 | isopropanol | 250 | 1/6 | 65.0 | 72.8 |
| 37 | isopropanol | 300 | 1/6 | 80.2 | 38.2 |
| 38 | ethylbezene | 300 | 1/30 | 45.5 | 85.0 |
| 39 | ethylbenzene | 350 | 1/60 | 37.9 | 81.9 |
| 40 | n-dodecane | 370 | 1/120 | 35.0 | 80.5 |

EXAMPLE 41

0.25 parts of cis-5-(2-furyl)-3-methyl-2-pentenal of the following formula

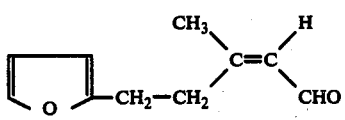

was reacted at 150° C. for 3 hours in an atmosphere of nitrogen using 1 part of substantially anhydrous isopropanol as a solvent and 1 mole%, based on the pentenal, of phthalic acid as a catalyst.

After the reaction, the reaction mixture was subjected to gas chromatography in the same way as in Examples 2 to 13, and the conversion and selectivity were determined. It was found that the cis-isomer was isomerized to the corresponding trans-isomer at a conversion of 54.5% and a selectivity of 89.0%. The results are shown in Table 6.

EXAMPLE 42

The procedure of Example 41 was repeated except that the α,β-unsaturated aldehyde shown in Table 7 was used instead of the cis-5-(2-furyl)-3-methyl-2-pentenal. The results are shown in Table 7.

Table 7

| Example | α,β-unsaturated aldehyde | Conversion of cis-isomer (%) | Selectivity of trans-isomer (%) |
|---|---|---|---|
| 42 | 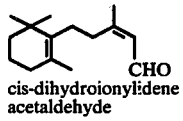 cis-dihydroionylidene acetaldehyde | 32.0 | 92.0 |

EXAMPLES 43 TO 52

0.25 part of cis-citral was reacted at 150° C. for 3 hours in an atmosphere of nitrogen using 1 part of each of the various substantially anhydrous solvents indicated in Table 8 and 1 mole%, based on the cis-citral, of phthalic acid as a catalyst. The reaction mixture was analyzed for the conversion of cis-citral and the selectivity of trans-citral, and results are shown in Table 8.

Table 8

| Example | Solvent | Conversion of cis-citral (%) | Selectivity of trans-citral (%) |
|---|---|---|---|
| 43 | Benzene | 59.6 | 90.1 |
| 44 | Ethyl acetate | 41.0 | 99.5 |
| 45 | Chlorobenzene | 59.3 | 83.0 |
| 46 | Cyclohexane | 58.0 | 91.6 |
| 47 | n-Hexane | 56.6 | 92.4 |
| 48 | Methyl ethyl ketone | 45.8 | 89.7 |
| 49 | Perchloroethylene | 58.9 | 84.7 |
| 50 | Dioxane | 30.8 | 89.3 |
| 51 | Chloroform | 62.8 | 82.6 |
| 52 | Not used | 64.4 | 72.8 |

EXAMPLES 53 TO 60

0.25 part of trans-citral was reacted at 150° C. for 3 hours in an atmosphere of nitrogen using 1 part of each of the substantially anhydrous solvents indicated in Table 9 and 1 mole%, based on the trans-citral, of phthalic acid. The resulting reaction mixture was analyzed for the conversion of trans-citral and the selectivity of cis-citral, and the results are shown in Table 9.

Table 6

| Structure | B.P. ° C./mmHg | High-mass data Calculated | High-mass data Found | Infrared spectrum (Specific absorption) (cm$^{-1}$) | NMR spectrum (specific absorption) τ value | NMR spectrum (specific absorption) H number |
|---|---|---|---|---|---|---|
| 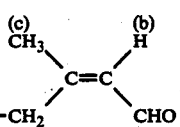 cis-5-(2-furyl)-3-methyl-2-pentenal | 75/0.25 | C$_{10}$H$_{12}$O$_2$ 164.0837 | C$_{10}$H$_{12}$O$_2$ 164.0832 | $v_{c=o}$ 1673 $v_{c=c}$ 1633 1613 | H(a) 0.18 / 0.26 H(b) 4.10 / 4.18 H(c) 8.06 | 1 / 1 / 3 |
| 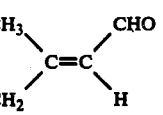 trans-5-(2-furyl)-3-methyl-2-pentenal | 76/0.26 | 164.0837 | 164.0825 | $v_{c=o}$ 1673 $v_{c=c}$ 1633 1613 | H(a) 0.04 / 0.04 H(b) 4.10 / 4.18 H(c) 7.86 | 1 / 1 / 3 |

Table 9

| Example | Solvent | Conversion of trans-citral (%) | Selectivity of cis-citral (%) |
|---|---|---|---|
| 53 | Perchloroethylene | 37.6 | 92.0 |
| 54 | Benzene | 33.4 | 95.5 |
| 55 | Ethyl acetate | 29.2 | 94.2 |

Table 9-continued

| Example | Solvent | Conversion of trans-citral (%) | Selectivity of cis-citral (%) |
|---|---|---|---|
| 56 | Chlorobenzene | 35.3 | 92.4 |
| 57 | Cyclohexane | 35.6 | 96.6 |
| 58 | n-Hexane | 36.0 | 95.0 |
| 59 | Methyl ethyl ketone | 29.1 | 86.6 |
| 60 | Not used | 46.6 | 62.2 |

EXAMPLES 61 AND 62

0.25 part of cis-citral was reacted at 150° C. for 3 hours using 1 part of isopropanol of different water contents as a solvent and 1 mole%, based on the cis-citral, of phthalic acid as a catalyst. The resulting reaction product was analyzed for the conversion of cis-citral and the selectivity of the trans-citral, and the results are shown in Table 10.

Table 10

| Example | Water content of isopropanol (% by weight) | conversion of cis citral (%) | Selectivity of trans-citral (%) |
|---|---|---|---|
| 61 | 10 | 55.1 | 84.2 |
| 62 | 15 | 63.0 | 83.3 |

Comparative Examples 1 to 5

In these comparative runs, acid catalysts having a pKa outside the range of 1 to 7 were used.

0.25 part of each of the $\alpha,\beta$-unsaturated aldehydes indicated in Table 11 was reacted at 150° C. for 3 hours using 1 part of substantially anhydrous isopropanol as a solvent and 1 mole%, based on the $\alpha,\beta$-unsaturated aldehyde, of each of the acid catalysts indicated in Table 11. The resulting reaction mixtures were each analyzed for the conversion and selectivity. The results are shown in Table 11.

Table 11

| Comparative Ex. | Catalyst Kind | pKa | $\alpha,\beta$-unsaturated aldehyde | Conversion (%) | Selectivity (%) |
|---|---|---|---|---|---|
| 1 | p-Toluene | 0.6 | cis-citral | 100 | 0 |
| 2 | Sulfuric acid | −3 | cis-citral | 100 | 0 |
| 3 | p-Toluene-sulfonic acid | 0.6 | trans-citral | 99.8 | 0 |
| 4 | Sulfuric acid | −3 | trans-citral | 99.8 | 0 |
| 5 | p-Bromophenol | 8.25 | trans-citral | 3.9 | 60 |

The above procedure in Comparative Examples 1 to 5 was repeated except that the reaction time was changed to 1 hour. The conversions were much the same as those shown in the above table, and the selectivities were nearly zero.

What we claim is:

1. A process for isomerizing one of the geometric isomers of an $\alpha,\beta$-unsaturated aldehyde to the corresponding other geometric isomer, which comprises heating an $\alpha,\beta$-unsaturated aldehyde of the formula

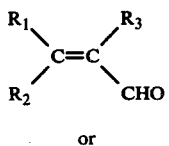

(1-A)

or

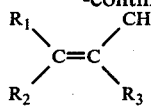

(1-B)

wherein
$R_1$ is alkyl of 1 to 30 carbon atoms or alkenyl of 2 to 30 carbon atoms, and
$R_2$ and $R_3$, independently of each other, are hydrogen or alkyl of 1 to 5 carbon atoms,
each of said alkyl and alkenyl represented by $R_1$, $R_2$ and $R_3$, independently of one another, being unsubstituted or substituted by 1 to 3 substituents selected from the group consisting of alkoxy of 1 to 5 carbon atoms, alkoxycarbonyl of 2 to 6 carbon atoms, fluorine, chloride and bromine,
with the proviso that $R_2$ is different from $R_1$,
at a temperature of 30 to 400° C. in the presence of an inert organic solvent which dissolves the $\alpha,\beta$-unsaturated aldehyde or is miscible with the aldehyde, and in the presence of (1) a catalyst having a pKa of 1 to 7, which is soluble in the reaction system, selected from the group consisting of hydrofluoric acid, nitrous acid, chromic acid, selenic acid, telluric acid, hypophosphorous acid, phosphorous acid, phosphoric acid, a partial ester of one of said acids which are polybasic, an organic carboxylic acid of 1 to 10 carbon atoms, and a partial ester of one of said organic carboxylic acids which are polybasic, or (2) as catalyst, a cation-exchange resin having a carboxyl group as an acid site and having a pKa of 1 to 7.

2. The process of claim 1 wherein the catalyst has a pKa of 1.2 to 6.

3. The process of claim 1 wherein the isomerization temperature is 30° to 350° C.

4. The process of claim 1 wherein the isomerization temperature is 40° to 300° C.

5. The process of claim 1 wherein the isomerization temperature is 50° to 250° C.

6. The process of claim 1 wherein the inert solvent is an organic solvent containing 1 to 15 carbon atoms selected from the group consisting of aliphatic hydrocarbons, alicyclic hydrocarbons, aromatic hydrocarbons, halogenated hydrocarbons, ethers, esters, ketones and alcohols.

7. The process of claim 1 wherein the inert solvent is an organic solvent containing 1 to 15 carbon atoms selected from the group consisting of aliphatic hydrocarbons, alicyclic hydrocarbons, aromatic hydrocarbons, alcohols and esters.

8. The process of claim 1 which further comprises separating the isomerization mixture obtained by the heating step into the constituent geometric isomers.

9. The process of claim 1 wherein the catalyst is selected from the group consisting of the phosphorous acid, the partial ester of phosphorous acid, the phosphoric acid, the partial ester of phosphoric acid, the hypophosphorous acid, the organic carboxylic acid of 1 to 10 carbon atoms, the partial ester of one of said organic carboxylic acids which are polybasic, and the cation-exchange resin having a carboxyl group as an acid site.

10. A process for isomerizing one of the geometric isomers of an $\alpha,\beta$-unsaturated aldehyde to the corresponding other geometric isomer, which comprises heating an α,β-unsaturated aldehyde selected from the group consisting of 2-methy-3-furyl-acrolein, 2-ethyl-3-furyl-acrolein, 2-propyl-furyl-acrolein, 3-methyl-4-furylidene-butyraldehyde and 5-(2-furyl)-3-methyl-2-pentenal, at a temperature of 30° to 400° C. in the presence of an inert organic solvent which dissolves the α,β-unsaturated aldehyde or is miscible with the aldehyde, and in the presence of (1) a catalyst having a pKa of 1 to 7, which is soluble in the reaction system, selected from the group consisting of hydrofluoric acid, nitrous acid, chromic acid, selenic acid, telluric acid, hypophosphorous acid, phosphorous acid, phosphoric acid, a partial ester of one of said acids which are polybasic, an organic carboxylic acid of 1 to 10 carbon atoms, and a partial ester of one of said organic carboxylic acids which are polybasic, or (2) as catalyst, a cation-exchange resin having a carboxyl group as an acid site and having a pKa of 1 to 7.

11. The process of claim 10 wherein the catalyst is an acid having a pKa of 1.2 to 6.

12. The process of claim 10 wherein the isomerization temperature is 30° to 350° C.

13. The process of claim 10 wherein the isomerization temperature is 40° to 300° C.

14. The process of claim 10 wherein the isomerization temperature is 50° to 250° C.

15. The process of claim 10 wherein the inert solvent is an inert organic solvent containing 1 to 15 carbon atoms selected from the group consisting of aliphatic hydrocarbons, alicyclic hydrocarbons, aromatic hydrocarbons, alcohols and esters.

16. The process of claim 10 wherein the catalyst is selected from the group consisting of the phosphorous acid, the partial ester of phosphorous acid, the phosphoric acid, the partial ester of phosphoric acid, the hypophosphorous acid, the organic carboxylic acid of 1 to 10 carbon atoms, the partial ester of one of said organic carboxylic acids which are polybasic, and the cation-exchange resin having a carboxyl group as an acid site.

* * * * *